(12) United States Patent
Ling et al.

(10) Patent No.: US 8,932,978 B2
(45) Date of Patent: Jan. 13, 2015

(54) PHOTOCATALYST COMPOSITION AND PREPARATION FOR THE SAME

(75) Inventors: Yong-Chien Ling, Hsinchu (TW); Jen-Yu Liu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 24 days.

(21) Appl. No.: 13/425,489

(22) Filed: Mar. 21, 2012

(65) Prior Publication Data
US 2013/0253073 A1    Sep. 26, 2013

(51) Int. Cl.
*B01J 27/24* (2006.01)
*B01J 23/00* (2006.01)

(52) U.S. Cl.
USPC ........... 502/200; 502/201; 502/300; 502/314; 502/340; 502/344

(58) Field of Classification Search
USPC .................. 502/200, 201, 300, 314, 340, 344
See application file for complete search history.

(56) References Cited

U.S. PATENT DOCUMENTS

| | | | | | |
|---|---|---|---|---|---|
| 1,885,027 | A | * | 10/1932 | Patterson | 524/432 |
| 4,344,909 | A | * | 8/1982 | De Blauwe | 264/230 |
| 5,690,922 | A | | 11/1997 | Mouri et al. | |
| 6,191,062 | B1 | * | 2/2001 | Hayakawa et al. | 502/159 |

OTHER PUBLICATIONS

Zhang et al., Significantly improved photocatalytic hydrogen production activity over Cd1-xZnxS photocatalysts prepared by a novel thermal sulfuration method, Nov. 1, 2007, International Journal of Hydrogen Energy, vol. 32, pp. 4685-4691.*
Maeda et al., "GaN:ZnO Solid Solution as a Photocatalyst for Visible-Light-Driven Overall Water Splitting", 2005, J. Am. Chem. Soc., vol. 127No. 23, pp. 8286-8287.*
Liu, J.Y., Gary, B. and Ling, Y. C. "CuxAgyInzZnkSm solid solutions customized with RuO2 or Rh132CrO.660J co-catalyst display visible light-driven catalytic activity for CO2 reduction to CH3OH". Green Chem. 2011, 13,2029-2031.

* cited by examiner

*Primary Examiner* — Ali Soroush
(74) *Attorney, Agent, or Firm* — Gottlieb, Rackman & Reisman, P.C.

(57) ABSTRACT

A solid solution photocatalyst composition and its preparation method are provided in the present invention. The solid solution photocatalyst can utilize its solid solution structure to regulate the conduction band position, valence band position, conduction band range and valence band range of the different response properties of the photocatalyst, so that oxidoreductive reaction is performed to remove the foul-smelling substances.

16 Claims, No Drawings

PHOTOCATALYST COMPOSITION AND PREPARATION FOR THE SAME

FIELD OF THE INVENTION

The present invention relates to a photocatalyst composition, in particular to a solid solution photocatalyst composition and the preparation thereof. The solid solution photocatalyst composition utilizes its solid solution to regulate a conduction band position, a valence band position, a conduction band range and a valence band range of different photocatalytic reaction characteristics for removing the odorous substances.

BACKGROUND OF THE INVENTION

There are variety of compounds releasing unpleasant smell to the surrounding in the living environment and even harmful to human health, which compounds such as ammonia, amine, hydrogen sulfide, mercaptan, short chain fatty acid, aldehyde, etc. are typical compounds relate to stench in the kitchen, toilet, basement and car. At present, there has developed many types of deodorant to deodorize or absorb these stenches. The deodorant supplied in the market usually covers up the stench by releasing air freshener, proceeding physical absorption and having a chemical reaction with stench compounds. The substance used as a absorbent including activated carbon, zeolite, cyclodextrin, bentonite, etc. The material having chemical reaction with stench compounds usually including a chlorine dioxide, a hypochlorous acid, an ozone and a polymer contains function groups, and these materials decompose the stench compounds by oxidation, reduction or neutralization.

The common photocatalyst is nano-titanium dioxide photocatalyst since 1990s, when the nano-titanium dioxide photocatalyst exposed to light, it will produce photocatalytic reaction continuously, and produces a hydroxyl radical having function of decomposing organic matter, and inhibiting virus activity, etc., but does not consume itself The scientist applies the nano-titanium dioxide photocatalyst which results in good effect in air purification, antibiotic, deodorization, sterilization and anti-mold. However, the light wavelength absorbed by common photocatalyst usually is UV or visible light. Therefore, in response to diverse demands, it requires a photocatalyst capable of absorbing visible light and/or UV, and arbitrarily regulating the absorption of light in the wavelength range.

U.S. Pat. No. 5,690,922 discloses a deodorizing fiber, which contains a phosphorus-containing tetravalent metal, a hydroxide-containing divalent metal and a reactive oxygen species produced by exposing to light, and served as a photocatalyst of the photo-oxidation catalyst. The photocatalyst is composed of a variety of light semiconductors, and can be a metal or a nonmetal including sulfur-containing semiconductor, chalcogenide compounds, oxygen-containing semiconductor, etc., where the deodorant fiber has deodorant effect against acidic, alkaline and neutral stench molecular under the sunlight, fluorescent lamp and UV lamp. However, the photocatalyst is formed by two or three combinations of metals, and does not have a function of regulating the absorption of light wavelength range.

The conduction band and valence band position of the fixed composition of the photocatalyst, such as titanium dioxide, is fixed. The conduction band of the semiconductor plays the deliver role for a negatively charge, the valence band of the semiconductor plays the deliver role for a positive charge, and the different position of conduction band and valence bond will affect different chemical reactions (because of the difference of its reaction potential, for example the more difficult response to restore, the higher conduction band position is required). The physical and chemical properties of solid solution photocatalyst can be tuned by changing its component. Hence, the position and the range of the conduction band and valence band of the solid solution photocatalyst can be regulated. Usually the high conductivity photocatalyst and the low conduction band photocatalyst are synthesized to form a middle conduction band photocatalyst, and valence band is formed by the same way.

Therefore, it becomes an important issue for seeking a photocatalyst capable of controlling the conduction band position, valence band position, conduction band range and/or valence band range, so that the photocatalyst can regulate the wavelength range of the absorbed light.

It is therefore attempted by the applicant to deal with the aforementioned situation encountered in the prior art.

SUMMARY OF THE INVENTION

As to the idea of a controlled absorption of the light wavelength range, the present invention provides a solid solution photocatalyst. The solid solution photocatalyst can utilize its solid solution structure to regulate the conduction band position, valence band position, conduction band range and valence band range of the different response properties of the photocatalyst, so that having the absorption of a range of 10 nm to 14,000 nm wavelength of light for proceeding oxidoreductive reaction to remove the stench compounds. The metal structure in the solid solution structure reacts with the stench compounds containing nitrogen and sulfur atom. From the aspects of manufacturing, using and cleaning, the solid solution photocatalyst of the present invention can improve the environment and can be recycled.

Therefore, the present invention provides a photocatalyst composition including a solid solution photocatalyst. The photocatalyst composition further includes a carrier and an additive.

Preferably, the photocatalyst composition is used as deodorization, sterilization, anti-mold and scavenging air, wherein the solid solution photocatalyst is a crystal structure, and the crystal structure is one selected from a group consisting of a metal oxide, a metal sulfide, a metal nitride, a non-metal oxide, a nonmetal sulfide, a nonmetal nitride and a combination thereof. The photocatalyst composition also has a photocatalyst reaction for regulating at least one of a conduction band position, a valence band position, a conduction band range and a valence band range, and for absorbing a light having a wavelength within a range of 10 nm to 14,000 nm for proceeding an oxidoreductive reaction.

Preferably, the photocatalyst composition is connected with a matrix, and the matrix is one selected from a group consisting of a hexose, a glucose, a starch, a cellulose and a combination thereof.

The present invention further provides a preparation method of a solid solution photocatalyst, including steps of: (a) diluting an element in a deionization water; (b) adding a chelating agent into the deionization water for forming a salt solution; (c) adding a sulfur-containing substance, and one of an oxygen-containing substance and a nitrogen-containing substance into the salt solution to obtain a mixed solution; and (d) drying the mixed solution to obtain the solid solution photocatalyst.

The present invention further provides a preparation method of a photocatalyst composition, including steps of: (a) providing a solid solution photocatalyst; (b) mixing the solid solution photocatalyst with an additive to form a premixture; and (c) placing the premixture on a carrier.

The present invention further provides a solid solution photocatalyst, including: a metal material having a first crystal phase; and a nonmetal material having a second crystal phase, wherein the second crystal phase is embedded with the first crystal phase to obtain a solid solution, and the nonmetal material is one selected from a group consisting of a sulfur-containing substance, an oxygen-containing substance and a nitrogen-containing substance.

The above objectives and advantages of the present invention will become more readily apparent to those ordinarily skilled in the art after reviewing the following detailed descriptions.

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

The present invention provides a photocatalyst composition, including 0.005 to 10% by weight of a solid solution photocatalyst, wherein the solid solution structure is selected from a various kind of positively charged oxides, sulfides or nitrides of metal or non-metal elements of copper, zinc, silver, platinum, nickel, iron, etc., and using its crystal structure configured for matching solid solution structure as well as their mixtures.

The solid solution structure of the present invention is a solid state solvent, which is constituted by one or more solute dissolved in the solvent. The structure is considered as a homogeneous single-phase, and changed by the types and the proportion of the element which involved in the reaction. The crystal compound considered as the solid solution structure must have the following characteristics: (a) the same crystal structure; (b) the similarity of the atomic radius of the constituent element; (c) the similarity of the atomic chemical property of the constituent element; (d) the correspondence of the positive and negative charge of the valence state; (e) the similarity of the atomic electron affinity of the constituent element. The physical and chemical property of the solid solution structure of the present invention is changed by regulating the constituent element of the photocatalyst, such as the wavelength range of the absorption light. Compared to the traditional photocatalyst can only absorb a specific wavelength range of light, the photocatalyst of the present invention has more freedom in the regulation, and has better ability to cater for different needs.

The solid solution structure of the present invention further includes a carrier, and the carrier is a polymer which contains a material derived from renewable resources. The material is selected from water, ethanol, butanol, glycerol, 1,3-propylene glycol, 1,2-propylene glycol, sorbitol, xylitol, mannitol, maltitol, vegetable oil, partially neutralized cross-linked polyacrylic acid and the combination thereof. The 1,3-propylene glycol is the best source, because it is obtained by fermentation of corn material. Due to the 1,3-propylene glycol does not deplete the fossil fuel, and releases its carbon into the atmosphere when degradation and be reused by the plant. Accordingly, using bio-derived 1,3-propylene glycol in the photocatalyst composition has smaller influence to the environment. Hence, compared with similar composition containing petroleum based diols, the composition of the present invention having environmental advantages.

The photocatalyst composition of the present invention includes a carrier or a carrier composition. The content in the composition owned 10% to 95% by weight, preferably 20% to 90% by weight. Moreover, the composition contains greater than 80% in the total weight of the composition derived from renewable resource ingredients.

The photocatalyst composition of the present invention contains an additive, including but not limited to the functional ingredients, the beneficial agent, the humectant and the moisturizer. In most of the embodiment, the photocatalyst composition of the present invention not only contains the solid solution photocatalyst but also contains the functional component which good for the user. The substances are generally known in the field of technical staff of the personal care composition, including but not limited to antibacterial agents and spices.

The functional component (and other components of the photocatalyst composition as described below) is classified according to the beneficial effects or presumed react mode. However, it should be understood that the functional components (and other ingredients) of the present invention provides more than one beneficial effects in some situation, or reacts through more than one react modes. Therefore, the classification of the present invention proceeds for convenience, and not only limited the active substance to one or more concrete application.

The substances used as the functional component in the photocatalyst composition of the present invention are listed as follows:

(1) a spice and an aromatic agent which causing olfactory response, and a deodorant spice which can reduce the body odor in addition to providing flavor;

(2) a cool agent, such as a menthol, a menthyl acetate, a pyrolidone Menthyl formate, a N-ehtyl-p-menthane-3-carboxamide and other menthol derivatives. The cool agent will cause tactile reaction by cool sense.

(3) a deodorant component different from spice and its function is to decrease or to eliminate the microbial on the surface of the skin, especially the microbial which causing the body odor produced.

(4) a powder, a pigment and a colorant; and (5) a medicament.

The other instances of the beneficial agent including an abrasive, an absorbent, an aesthetic component (e.g. a sunscreen and a pearl additive), an essential oil, a skin sensitizer, a cosmetics astringent and a drug astringent (e.g. a clove oil, a menthol, a camphor, a massage oil, an eugenol, a lactic acid menthyl and a hamamelis distillate liquid), an anti-acne agent (e.g. a resorcinol, a sulfur, a salicylic acid, a peroxide benzyl phthalate, an erythromycin and a zinc), an anti-caking agent, an anti-microbial agent (e.g. a butyl carbamate iodine propyl), an antioxidant (eg. a nicotinic acid tocopherol acetate), a cosmetic, an insecticide, a topical analgesic, a pH modifier (e.g. a citric acid, a sodium citrate, a succinic acid, a phosphoric acid, a sodium hydroxide and a sodium carbonate), a comfort and/or a rehabilitation agent (e.g. a panthenol and the derivative thereof such as an ethyl panthenol, an aloe, a pantothenic acid and the derivative thereof, an allantoin, a bisobolol and a dipotassium glycyrrhizate), a retinoid (e.g. a palm acid retinol ester), a care agent, a vitamin and the derivative thereof, and other similar substances.

The humectant has been described as an agent for regulating the exchange of moisture between the product and air in the container and environment. The humectant also been described as a compound in order to prevent a skin from drying and increase the water content of a skin surface (such as hygroscopic compound).

The suitable moisturizer includes hrdrophobic agent, hydrophilic agent and the combination thereof. The moisturizer includes a allantoin, a glycerol, a polyisobutylenyl triglyceride, a panthenol, a polyol, a ceramide, a borage oil (linoleic acid), a tocopherol (vitamin E), a linoleic acid, a tocopherol acetate, a polydimethyl siloxane, a hyaluronic acid, a pyrolidone carboxylic acid sodium (PCA-sodium), a wheat protein (e.g. lauryl dimethylamine hydroxypropyl hydrolyzed wheat protein), a hair keratin amino acid, an evening primrose oil, GLA 3 and other fish oil (e.g. linoleic acid) and linseed oil and the mixture thereof.

The other ingredients may also exist in the present invention except the above-captioned ingredient, including a gelling agent, a surfactant, an emulsifier and a preservative, or further including a fatty acid salt such as a stearic acid, a palm acid, a sodium or a potassium of an oleic acid or a linolenic acid, and the mixture thereof.

The other common ingredients in the personal care composition includes a preservative, wherein the preservative includes a methanol, a methyl 4-hydroxybenzoate, a propylparaben, a methylchloroisothiazolinone, a methylisothiazolinone, an imidazolidinyl urea, a phenoxyethanol, a sodium benzoate, and a benzoic acid. An EDTA and the salt thereof used in further enhance the corrosion resistance of the photocatalyst composition.

In addition, the photocatalyst composition includes 0.5 to 10% by weight, preferably 1 to 8% by weight of curing agent or gelling agent (e.g. sodium stearate). The photocatalyst composition includes 0.5 to 10% by weight, preferably 1 to 8% by weight of the emulsifier/solubilizer (e.g. poly(propylene ether) diacrylate).

The photocatalyst composition further includes one or various functional additives, including a fragrance agent and an antibacterial agent. In general, the content of fragrance agent between 0.1 to 3% by weight, preferably between 0.3 to 2.5% by weight. The fragrance agent could be an essential oil, such as a rosewood oil, a lavender oil, a lemon oil, a lime oil, a citrus oil, a rose oil, a coriander oil, a cypress oil, an orange oil and a pine oil. The amount of the antibacterial agent ranged between 0.1 to 0.5% by weight, preferably 0.2 to 1.5% by weight. The example of antibacterial agents are triclosan (5-chloro-2-(2,4-dichlorophenoxy) phenol) and CHLORA-CEL® sodium lactate chloroaluminum (Reheis, Inc., Berkeley Heights, N.J.).

The photocatalyst composition is connected to a matrix, the matrix includes but not limited to a hexose, a glucose, a starch, a cellulose and the combination thereof. The mechanism of deodorization:

First, analyzing the foul smell which mainly produced from the decomposition of component in the waste, generally divided into three categories:

The main component of the first category includes $NH_3$ and other nitrogenous compounds.

The second category includes $H_2S$, $SO_2$, which sulfur-contained odor gas. $H_2S$ is a colorless, irritating and suffocative toxic gas. The odor gas entered the body through the respiratory tract. After absorbing large amount of $H_2S$, will make people poison to dead which hazard to human. The moderate poison can lead pneumonia, it could cause coma, shock or reflex respiratory arrest in serious poison people. $SO_2$ is a colorless and irritating toxic gas, it could cause suffocation and coma in serious people.

The third category is an organic compound, such as organic acids, carbonhydrates, and sulfur-containing and nitrogen-containing compound, they also emit an unpleasant odor. Although the content of such compound is low, but toxicity is strong, and contains various substances causing carcinogenicity, deformity and mutagenicity which having a serious threat to human health.

According to the property and component of above-captioned foul smell gas, the present invention using the following technical to achieve the purpose of the present invention.

According to the physical properties of the photocatalyst composition, the surface thereof is hydrophilic. For example, the copper zinc sulfide can absorb polar materials such as $H_2S$ to make the odor-containing particles flocculation, and can be used as a flocculant. According to the chemical properties of the solid solution structure in the photocatalyst composition, the solid solution structure is of inorganic molecular having complex structure and oxidoreduction function. In contact with the pollutant, the photocatalyst composition can combine with nitrogen, sulfur, and oxygen atom of the odorous substance by its solid solution structure to form another photocatalyst. The most important, the solid solution structure photoctalyst composition contains different conduction band position, valence band position, conduction band range and valence band range, which determines its oxidation, reduction and provides stronger chelating ability, which played a special role in the deodorant.

The reaction process of removing the ammonia, nitrogen, $H_2S$ and $SO_2$ odorous substances by the solid solution structure photocatalyst composition is described as follows:

1. removing nitrogen-containing odor molecule, such as $NH_3$ and $NH_4^+$:

In nitrogen-containing odorous molecule, the odor of ammonia is very obvious. The solid solution structure photocatalyst composition (P) contacts with ammonia, and produces odourless ammonium or nitrate salt. The reactions are:

$$P+NH_3+0.5H_2O \rightarrow P+NH_4^+ +0.25O_2$$

$$P+NH_4^+ +3H_2O \rightarrow P+HNO_3+4.5H_2$$

$$HNO_3+P \rightarrow P-NO_3$$

2. removing nitrogen-containing odor molecule, such as NO and $NO_2$:

NO and $NO_2$ is the most prevalent air pollutant among nitrogen oxides. $NO_2$ is a corrosive gas which having irritation and toxicity ($NO_2+O_2 \rightarrow 2NO_2$). The water can be served as a solvent in the air and in the photocatalyst composition. According to the absorption, oxidation and nitrate formation of the photocatalyst, causing the deodorant effect is better. $NO_2$ will react with photocatalyst to yield a nitric acid.

$$P+NO_2+H_2O \rightarrow P+HNO_3+0.5H_2$$

$$HNO_3+P \rightarrow P-NO_3$$

3. removing $SO_2$:

$SO_2$ is a colorless, irritating toxic gas. The gaseous $SO_2$ will be soluble in the water ($SO_2+2H_2O \rightarrow H_2SO_3+H_2O$). Under general conditions, a volume of water can dissolve 40 volume of $SO_2$. According to the absorption, oxidation and sulfate formation of the photocatalyst, causing the deodorant effect is better.

$$P+H_2SO_3+H_2O \rightarrow P+H_2SO_4+H_2$$

$$H_2SO_4+P \rightarrow P-SO_4$$

4. removing $H_2S$:

(1) The content of $H_2S$ relates to the component of the landfill. When a large amount of organic substances corrupted in a landfill, the $H_2S$ will increase massively. When the solid solution photocatalyst of the present invention reacts with $H_2S$, then $H_2S$ is able to be removed.

The reaction is:

$$P+H_2S+4H_2O \rightarrow P+H_2SO_4+4H_2$$

$$H_2SO_4+P \rightarrow P-SO_4$$

(2) Using metal sulfides as an example of solid solution photocatalyst, the metal ion which dissolved and released from solid solution photocatalyst can chelate or generate salt with amino group, thiol group and oxygen group. For example, when the photocatalyst combine with $H_2S$ to form a sulfide precipitation rapidly, this reaction will remove harmful gas, which containing nitrogen and sulfur, rapidly and thoroughly.

5. removing odorous organic compounds:

The organic acid, carbohydrate and sulfur-containing, nitrogen-containing compound are produced from the organic compounds in the waste through the decomposition process of corruption. These compounds have active group, which will be oxidized and reduced by solid solution photocatalyst, and play a very important role in reducing a variety of pollution in the environment.

The preparation method of a copper silver indium silver zinc and sulfur photocatalyst of the present invention includes steps as follows:

Step 1: According to the stoichiometry ratio, dissolving the copper(I) chloride, silver nitrate, indium nitrate and zinc nitrate (Cu:Ag:In:Zn=1:1:1:7 or Cu:Ag:In:Zn=0.38:0.12: 0.5:1.0) in the deionized water, and adding chelating agent such as ammonium hydroxide to obtain a salt solution. The total concentration of the salt solution between 0.01 mol/L to 0.2 mol/L;

Step 2: Dissolving thioacetamide in the deionized water to obtain a thioacetamide solution. The concentration of the thioacetamide solution between 0.1 mol/L to 1 mol/L;

Step 3: The excess five times of the thioacetamide solution is dropped into stirring salt solution at the room temperature, and the dropping rate is between 0.01 mL/min to 2 mL/min. After dropping completely, it will continue stirring for at least 1 minute to obtain a mixed solution.

Step 4: Filtrating and washing the mixed solution, and putting it into an oven for drying 1 to 12 hours. After grinding can obtain the copper silver indium silver zinc and sulfur photocatalyst.

The preparation method of a photocatalyst composition of the present invention includes steps as follows:

Step 1: Preparation a photocatalyst which regulates a conduction band position, a valence band position, a conduction band range and a valence band range of different photocatalytic reaction characteristics, and absorbs a light having a wavelength within a range of 10 nm to 14,000 nm.

Step 2: Mixing the photocatalyt and an additive to form a premixture.

Step 3: Using the way of coating, dispersion and carrying to coat a carrier polymer or weave a carrier polymer to the mesh, for carrying the photocatalyst on the light permeably area and proceeding a reaction.

Step 4: The premixture is carried on the light permeably area of the carrier polymer overnight, wherein the weight ratio of the premixture and the carrier polymer is in a range of 1:200 to 1:1.

Embodiment 1

Weighting 1 gram of the solid solution photocatalyst, and adding a surfactant to disperse into a uniform photocatalyst solution, then sprayed onto a piece of paper containing 1% ammonia. After irradiating the photocatalyst solution by visible light, the odor of 1% ammonia is reduced.

Conclusion of the examination: the result of the experiment demonstrates that after using the solid solution photocatalyst of the present invention, a variety of odorous compound is effectively removed, and the removal ratio is more than 90%.

Embodiment 2

Spraying 1 gram of the solid solution photocatalyst to a glass which coating a polymer film, and then dropping a few drops of solution which containing 1% by weight of garlic. After irradiating by light, the odor is reduced significantly by many people with olfactory identification.

Conclusion of the examination: the result of the experiment demonstrates that after using the solid solution photocatalyst of the present invention, a variety of odorous compound is effectively removed, and the removal ratio is more than 90%.

Embodiment 3

Mixing 10 ppm of the ammonia (the urine smell in the public toilet has about 10 to 40 ppm of the ammonia) and the solid solution photocatalyst under the sunlight. After one hour, measuring the remained concentration of ammonia, and finding that the concentration of ammonia is only 1 ppm left. Therefore, it demonstrates that the solid solution photocatalyst can remove the odor of ammonia.

Conclusion of the examination: the result of the experiment demonstrates that after using the solid solution photocatalyst of the present invention, a variety of odorous compound is effectively removed, and the removal ratio is more than 90%.

While the invention has been described in terms of what is presently considered to be the most practical and preferred embodiments, it is to be understood that the invention needs not be limited to the disclosed embodiments. Therefore, it is intended to cover various modifications and similar configuration included within the spirit and scope of the appended claims, which are to be accorded with the broadest interpretation so as to encompass all such modifications and similar structures.

REFERENCES

1. U.S. Pat. No. 5,690,922 (Nov. 25, 1997).

What is claimed is:

1. A photocatalyst composition, comprising a solid solution photocatalyst, a carrier and an additive, wherein the solid solution photocatalyst comprises a metal nitride, and at least two metal materials, each of which comprises one selected from a group consisting of a metal oxide, a metal sulfide and a metal nitride.

2. The photocatalyst composition as claimed in claim 1, wherein the carrier is a polymer allowing a light to pass through for inducing a surface reaction of the photocatalyst, the polymer is one selected from a group consisting of a solid, a liquid and a combination thereof, the carrier is derived from a renewable material, and the metals are ones selected from a group consisting of a copper, a zinc, a silver, a platinum, a nickel, an iron, an indium and a combination thereof.

3. The photocatalyst composition as claimed in claim 1, wherein the additive is one selected from a group consisting of a functional component, a beneficial agent, a humectant, a moisturizer and a combination thereof.

4. The photocatalyst composition as aimed in claim 3, wherein the functional component is one selected from a group consisting of a spice, an aromatic agent, a menthol, a menthyl acetate, a pyrolidone menthyl formate, a menthol derivative, a deodorant component, a powder, a pigment and a colorant, a medicament and a combination thereof.

5. The photocatalyst composition as claimed in claim 3, wherein the beneficial agent is one selected from a group consisting of an abrasive, an absorbent, an aesthetic component, an essential oil, a skin sensitizer, a cosmetic astringent, a drug astringent, an anti-acne agent, an anti-caking agent, an anti-microbial agent, an antioxidant, a cosmetic, an insecticide, a topical analgesic, a pH modifier, a comfort, a rehabilitation agent, a retinoid, a vitamin and a derivative thereof. and a combination thereof.

6. The photocatalyst composition as claimed in claim 3, wherein the humectant is a compound to prevent skin from drying out and increase the water content of a skin surface.

7. The photocatalyst composition as claimed in claim 3, wherein the moisturizer is one selected from a group consisting of an allantoin, a glycerol, a polyisobutylenyl triglyceride, a panthenol, a polyol, a ceramide, a borage oil (linoleic acid), a tocopherol (vitamin E), a linoleic acid, a tocopherol acetate, a polydimethyl siloxane, a hyaluronic acid, a pyrolidone carboxylic acid sodium (PCA-sodium), a wheat protein, a hair keratin amino acid, an evening primrose oil, a fish oil, a linseed oil and a combination thereof.

8. The photocatalyst composition as claimed in claim 1, wherein the photocatalyst composition is utilized in one selected from a group consisting of a deodorization, a sterilization, an anti-mold, a scavenging air and a combination thereof.

9. The photocatalyst composition as claimed in claim 1, wherein the solid solution photocatalyst is a crystal structure, and the crystal structure is one selected from a group consisting of a metal oxide, a metal sulfide, a metal nitride, a nonmetal oxide, a nonmetal sulfide, a nonmetal nitride and a combination thereof.

10. The photocatalyst composition as claimed in claim 9, wherein each of the metal and the nonmetal is an element having a positive charge.

11. The photocatalyst composition as claimed in claim 1, wherein the solid solution photocatalyst has a photocatalytic reaction for regulating at least one of a conduction band position, a valence band position, a conduction band range and a valence band range, and for absorbing a light having a wavelength within a range of 10 nm to 14,000 nm for proceeding an oxidoreductive reaction.

12. The photocatalyst composition as claimed in claim 1, wherein the photocatalyst composition is connected with a matrix, and the matrix is one selected from a group consisting of a hexose, a glucose, a starch, a cellulose and a combination thereof.

13. A solid solution photocatalyst, comprising:
    at least three metal materials having a first crystal phase; and
    a nonmetal material having a second crystal phase, wherein each of the metal material and the nonmetal material is an element having a positive charge, the second crystal phase is embedded with the first crystal phase to obtain a solid solution, and the nonmetal material is a nitrogen-containing substance.

14. The photocatalyst composition as claimed in claim 6, wherein each of the comfort and the rehabilitation agent is one selected from a group consisting of a panthenol, an ethyl panthenol, an aloe, a pantothenic acid, an allantoin, a bisobolol, a dipotassium glycyrrhizate and a combination thereof.

15. The photocatalyst composition as claimed in claim 13, wherein the metal material is one selected from a group consisting of a copper, a zinc, a silver, a platinum, a nickel, an iron, an indium and a combination thereof.

16. The photocatalyst composition as claimed in claim 13, wherein the nonmetal material further comprises one selected from a group consisting of a sulfur-containing substance, an oxygen-containing substance and a nitrogen-containing substance.

* * * * *